(12) United States Patent
Kopelman et al.

(10) Patent No.: US 7,112,065 B2
(45) Date of Patent: Sep. 26, 2006

(54) METHOD FOR DEFINING A FINISH LINE OF A DENTAL PROSTHESIS

(75) Inventors: Avi Kopelman, Ramat Chen (IL); Eldad Taub, Reut (IL)

(73) Assignee: Cadent Ltd., Or Yehuda (IL)

( * ) Notice: Subject to any disclaimer, the term of this patent is extended or adjusted under 35 U.S.C. 154(b) by 492 days.

(21) Appl. No.: 10/623,707

(22) Filed: Jul. 22, 2003

(65) Prior Publication Data

US 2005/0080503 A1    Apr. 14, 2005

Related U.S. Application Data

(60) Provisional application No. 60/397,672, filed on Jul. 22, 2002.

(51) Int. Cl.
*A06C 5/11*    (2006.01)

(52) U.S. Cl. .................................................. 433/213

(58) Field of Classification Search ................ 433/213, 433/214, 218, 223
See application file for complete search history.

(56) References Cited

U.S. PATENT DOCUMENTS 4,937,928 A * 7/1990 van der Zel ............... 29/896.1

| 5,372,502 | A | 12/1994 | Massen et al. |
| 5,417,572 | A | 5/1995 | Kawai et al. |
| 5,880,962 | A | 3/1999 | Andersson et al. |
| 6,049,743 | A * | 4/2000 | Baba ........................ 700/163 |
| 6,409,504 | B1 | 6/2002 | Jones et al. |
| 6,575,751 | B1 | 6/2003 | Lehmann et al. |
| 2003/0207235 | A1* | 11/2003 | der Zel ....................... 433/223 |

FOREIGN PATENT DOCUMENTS

WO   WO 97/03622   2/1997
WO   WO 00/08415   2/2000

* cited by examiner

*Primary Examiner*—Cary E. O'Connor
(74) *Attorney, Agent, or Firm*—Nath & Associates PLLC; Gregory B. Kang; Derek Richmond

(57) ABSTRACT

A computer-based prosthodontic method is provided, for enabling a dental practitioner to define a finish line of a dental prosthesis of at least one tooth to be fitted over a tooth preparation. The method comprises the following steps: providing a three-dimensional (3D) digital data relating to the patient's dentition, the 3D data includes data representative of the surface topology of the preparation and its surroundings; generating first finish line data representative of at least a portion of the finish line and superimposing an image of the finish line on an image of the dentition; obtaining second finish line data determined on the basis of input received from a dental practitioner; and using the second finish line data to update the first finish line data and superimposing the updated data on the dentition image.

11 Claims, 4 Drawing Sheets

METHOD FOR DEFINING A FINISH LINE OF A DENTAL PROSTHESIS

This application claims benefit of U.S. Provisional Patent Application No. 60/397,672 filed Jul. 22, 2002, the entire contents of which are hereby incorporated by reference in their entirety.

FIELD OF THE INVENTION

This invention relates to the filed of prosthodontics.

BACKGROUND OF THE INVENTION

An artificial dental prosthesis such as a crown covers portions of a tooth surface and is normally fabricated away from the patient's mouth, in a lab, and then installed in the mouth by the dentist.

The artificial crowns are prepared based on a working cast (also known by the term "master cast"). It is on the cast that all the technical steps leading to the completed restoration must be performed. In preparing artificial crowns, best mechanical compatibility between the abutment tooth (hereinafter referred to as the preparation) and the crown is desired, to ensure complete imperviousness of the restored structure. Thus, the more precisely the working cast reproduces the anatomy of the mouth in the areas to be treated, the more accurate will be the spatial position as will be the static and dynamic relationships within the mouth after treatment. An accurate working cast is thus important to produce a biomechanically acceptable restoration.

The precision of the cast depends on several factors, including, inter alia, the accuracy of the impressions and wax bites, the material from which the cast is constructed, and the identification of the anatomic contours and of the finish line (also referred to at times by the term "chamfer line" and "marginal line"), etc.

The finish line, by definition, is the apical limit of the abutment tooth model (the "preparation") and the margin of the reconstruction must end on it, i.e. it represents the point of transition between the biologic and artificial parts.

Being able to identify the zone that is apical to the finish line in absolute precision is fundamentally important for two reasons: (1) it allows to define the preparation limit with certainty, and (2) being intact, it maintains the anatomic characteristics of that tooth.

According to current practice, after diagnosing that a patient needs a crown, the dentist cuts the tooth to be reconstructed and prepares two impressions and a wax bite of the patient's jaws. Based on the impressions, wax bite and on written instructions of the dentist, a technician prepares in a lab the corresponding cast, and the relevant tooth within the preparation is temporary separated from the plaster so that the area with the anatomic information (the area defining the anatomic contour) and the finish line are exposed. At this point, the finish line is manually marked by the lab technician in ink on the preparation, and this finish line is an important parameter used in constructing the crown. Alternatively, a virtual three-dimensional (3D) image of the working cast is obtained e.g. in a manner as described in international publication No. WO97/03622, or in international publication No. WO00/08415, and the lab technician marks the finish line in the three dimensional environment.

U.S. Pat. No. 5,417,572 discloses a computer-based method for extracting a finish line for designing an artificial crown. Amounts of variation of data representing the shape of an abutment tooth are determined, and a train of points is extracted from the amounts of variation. Then a developed view of the surface shape of the abutment tooth is displayed, and the obtained train of points is also displayed in the developed view. The finish line for designing the artificial crown is determined, based on thus displayed train of points.

There are times when the finish line is not clear and the transition between the cut area to the biological area is not well defined. In such cases the technician either estimate himself where the line is or returns the cast (or the 3D virtual model) to the dentist for him to complete the finish line. In other cases, the boundaries between the cut area and the natural area of the tooth are blurred such that only the dentist himself is able to assess the cut area (the so-called 'knife edges'), and to define the finish line.

SUMMARY OF THE INVENTION

According to one of its aspects, the present invention provides a computer-based prosthodontic method for enabling a dental practitioner (e.g. a dentist) to define a finish line of a dental prosthesis of at least one tooth to be fitted over a tooth preparation, comprising:

(a) providing a three-dimensional (3D) digital data relating to the patient's dentition, the 3D data includes data representative of the surface topology of said preparation and its surroundings;

(b) generating first finish line data representative of at least a portion of said finish line and superimposing an image of said finish line on an image of said dentition;

(c) obtaining second finish line data determined on the basis of input received from a dental practitioner; and (d) using said second finish line data to update said first finish line data and superimposing the updated data on the dentition image.

The updating of the first finish line data comprises defining a portion of the finish line not defined in the first finish line data or changing a portion of said first finish line data.

According to another aspect, the present invention provides a computer-based method for constructing a crown to be fitted on a tooth preparation in a subject. The method comprises defining a finish line on the preparation to obtain finish line data and employing the finish line data in constructing the crown. The finish line is determined in a manner as defined above.

The present invention is best implemented over a computer network. Thus, according to yet another aspect, the present invention provides a computer-based system for enabling a dental practitioner to define a finish line of a dental prosthesis of at least one tooth to be fitted over a tooth preparation. The system comprises one or more central server utilities and a plurality of practitioner computerized machines connected to the server utility through a computer network, e.g. through the Internet.

Said server utility comprises:

(a) a processor;

(b) a memory coupled to the processor for storing a three-dimensional (3D) digital data relating to the patient's dentition, the 3D data including data representative of the surface topology of the preparation and its surroundings;

(c) a dedicated utility coupled to or integrated with the processor for generating a first finish line data representative of at least a portion of said finish line and superimposing an image of said finish line on an image of said dentition;

(d) a network interface coupled to the processor for transmitter to a dental practitioner computerized device at least a portion of the 3D digital data and the first finish line data and for receiving from the practitioner device data representative of a second finish line determined on the basis of practiotioner input, wherein the second finish line data is used to update the first finish line data.

Said practitioner machine comprises:

(a) a processor;
(b) a display coupled to the processor for presenting digital data relating to the patient's dentition, the digital data includes data representative of the surface topology of the preparation and its surroundings and a first finish line data representative of at least a portion of a finish line, such that the first finish line data is superimposed on the dentition image;
(c) a user interface coupled to the processor for allowing entry of a dental practitioner input for the determination of a second finish line data, the second finish line data being used to update the first finish line data; and
(d) a communication port coupled to the processor for receiving said digital data from a remote server utility and for conveying to the remote utility data relating to said updated first finish line data.

BRIEF DESCRIPTION OF THE DRAWINGS

In order to understand the invention and to see how it may be carried out in practice, preferred embodiments will now be described, by way of non-limiting examples only, with reference to the accompanying drawings, in which.

DETAILED DESCRIPTION OF THE INVENTION

Figure 1:
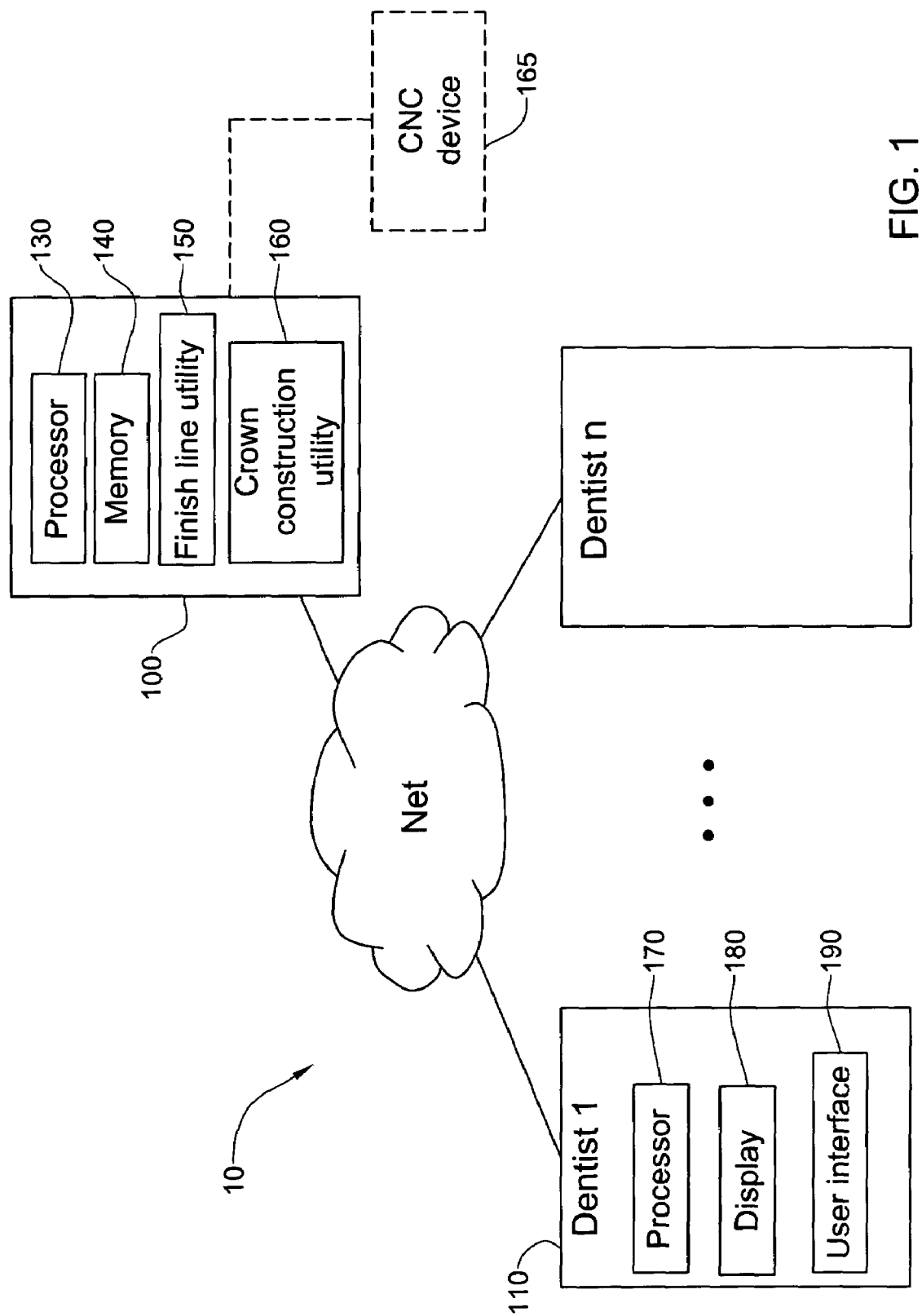
FIG. 1 shows, by way of a block diagram, a generalized system architecture in accordance with an embodiment of the invention.

The present invention provides a prosthodontic method that permits a dental practitioner (e.g. a dentist) to define a finish line on a tooth preparation. FIG. 1 is a general and schematic illustration of a computer-based system in accordance with an embodiment of the present invention. The system 10 includes a server computer 100 and a number of client machines such as 110, which can be personal computers. Each client computer communicates to the server computer 100 through a computer network 120 (e.g. Internet, Intranet) or through a dedicated communication link.

The server 100 includes, inter alia, a processor 130 and memory 140, which is coupled to the processor 130 for storing a three-dimensional (3D) digital data relating to the patient's dentition. The 3D data includes data representative of the surface topology of the preparation and its surroundings. A software utility 150 is further coupled to processor 130 or integrated with it, for generating data representative of at least a portion of said finish line.

Rather than drawing or marking by a lab technician the finished line on a working cast or in the virtual 3D environment, the finish line is generated in the service center 100 and is conveyed, via the computer network 10, to the dentist 1 computer 110. Computer 110 includes, inter alia, a processor 170, a display 180 and a user interface 190 for allowing presentation of the dentition image and for allowing entry of the dentist input regarding the finish line, for updating the digital data. The updated data is then conveyed back to the service center 100 and is used by the crown construction utility 160 for the digital and physical construction of the desired crown. The construction and fabrication of the crown can be done in a CAD/CAM (Computer-aided-design/Computer-aided-Manufacture) environment, utilizing for example, a CNC (Computer Numerical Control) device.

Figure 2:
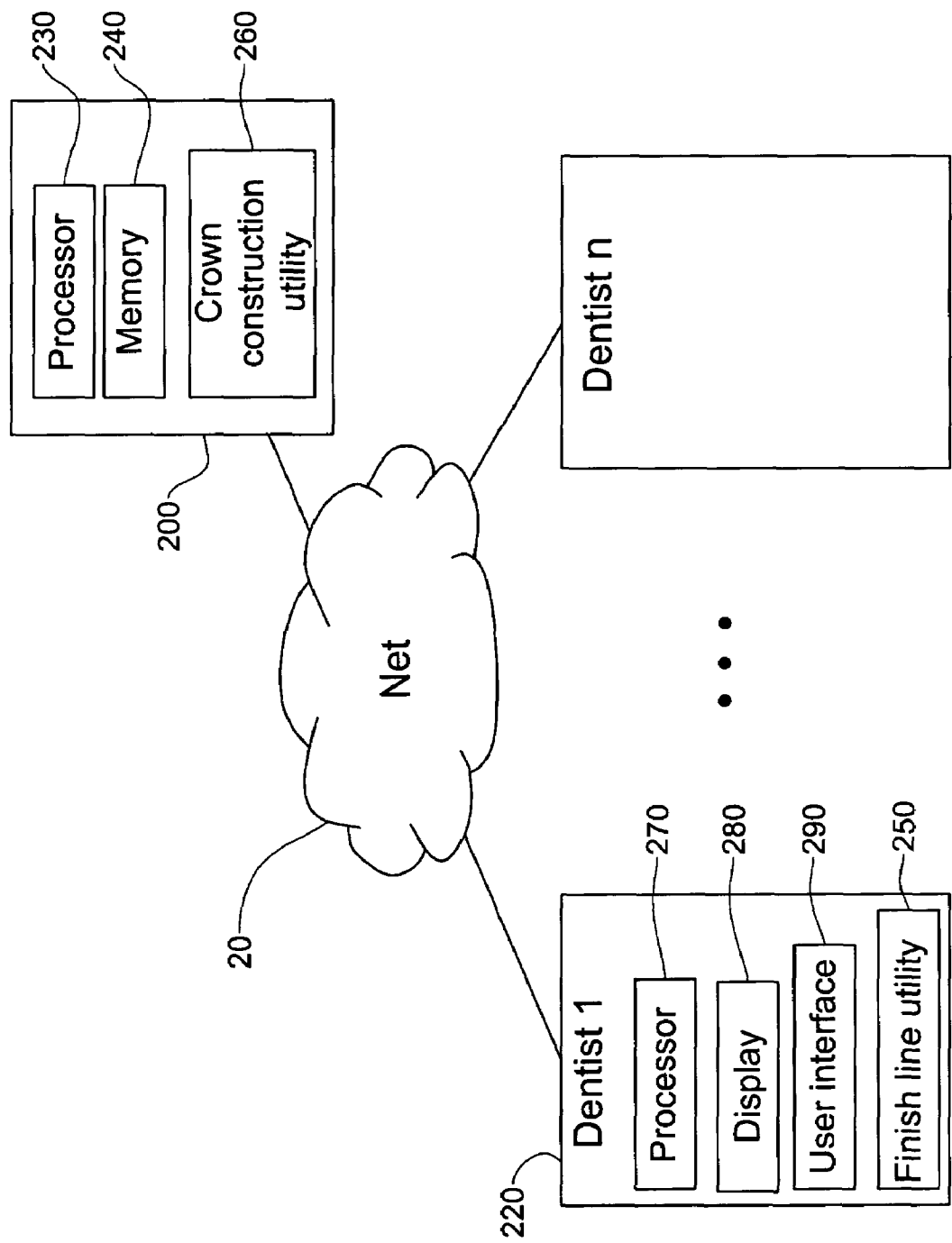
FIG. 2 shows, by way of a block diagram, a generalized system architecture in accordance with another embodiment of a system of the invention.

The present invention is not limited to the exemplary architecture of FIG. 1 and other configurations can be implemented, for example as described in FIG. 2 in which like components to those shown in FIG. 1 are given same reference numerals shifted by 100. The main difference between the system 20 of FIG. 2 and system 10 of FIG. 1 is that the finish line utility 250 is integrated in the client computer. Such architecture, for example, allows the dentist (or his assistant) to obtain at the clinic, the 3D data that relates to the patient's dentition. The dentist is then able to view 'on the spot', an image of the patient's dentition and to define the finish line immediately or at a later stage. According to this scenario, the service center 200 is provided with the 3D data of the patient's dentition including the definition of the finish line. This data is then used to construct the crown.

In both examples, the service center is provided with a finish line that is best defined by the dentist in accordance with his professional considerations, in a novel and a very efficient manner, without the need for further iterations between the lab technician and the dentist, as typically occurring in the hitherto working methodology.

Figure 3:
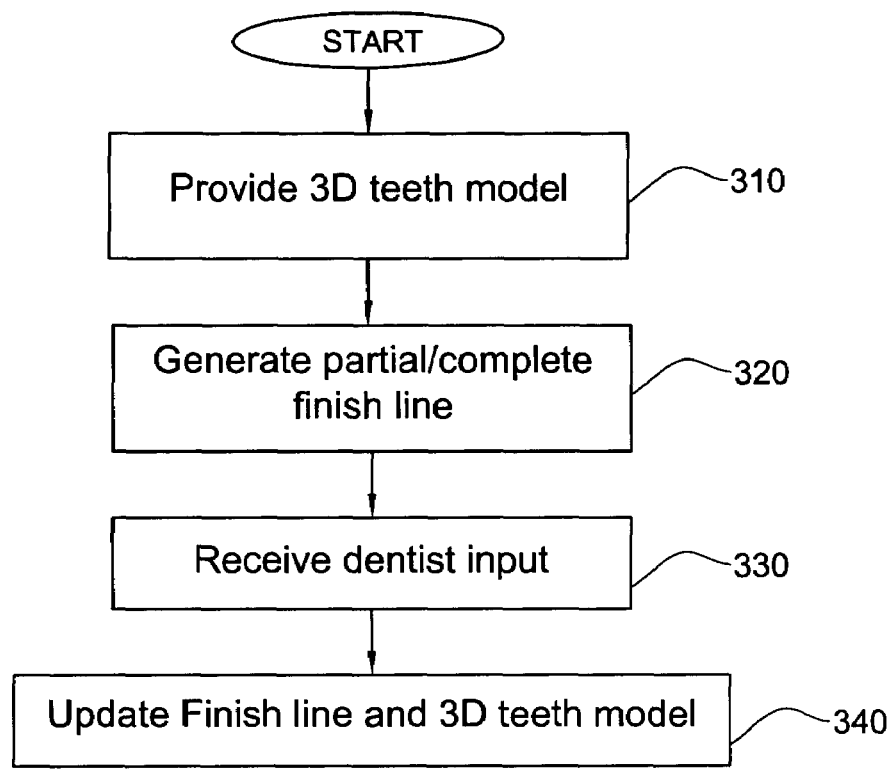
FIG. 3 is a schematic flow chart of a method for defining and displaying a finish line in accordance with an embodiment of the invention.

Reference is now being made to FIG. 3 showing, by way of a schematic blocked diagram, the steps for defining a finish line in a virtual three-dimensional teeth model. Following start, in step 310 a 3D teeth model of at least a portion of the teeth that includes the tooth preparation on which a crown is to be constructed is inputted. Then at 320 a first finish line is generated on the tooth preparation in a manual or a semi-automated or a fully automated manner. The first finish line is superimposed on the dentition image and is displayed on a suitable display medium.

Figure 4:
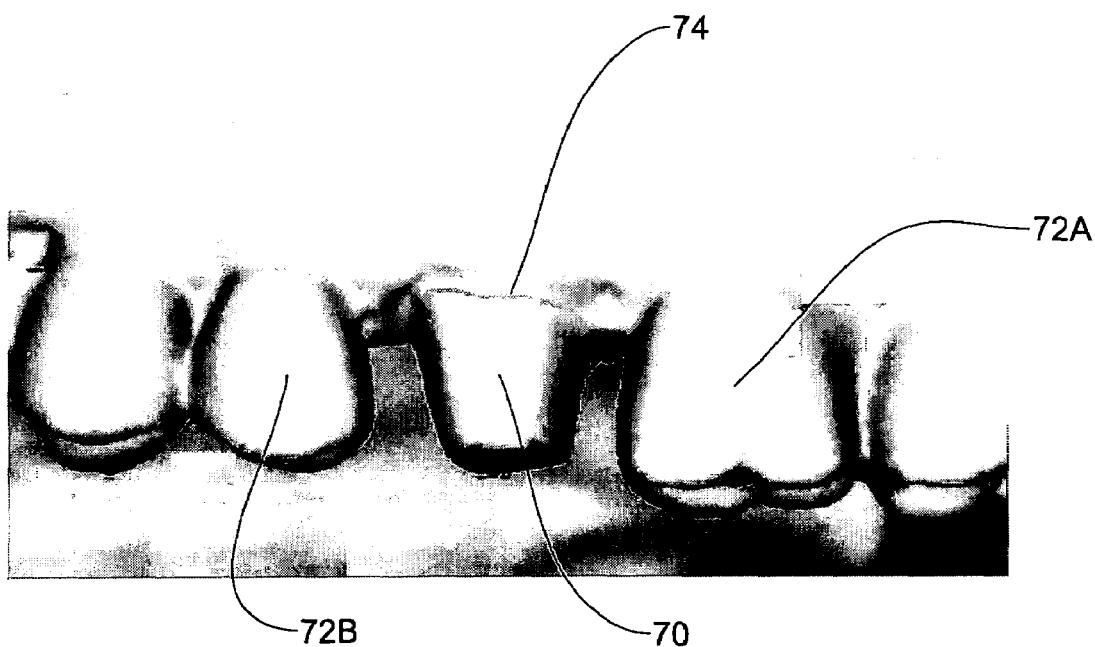
FIG. 4 shows a three-dimensional virtual image constructed in accordance with the invention with a finish line shown on the applicable portion of a tooth preparation.

FIG. 4 shows an example of such a display. A tooth preparation 70 is seen with its neighboring teeth 72A and 72B with a finish line 74 drawn as a continuous line on the apical limit of tooth preparation. In addition to general physical structure of such a teeth model, the colors of the neighboring teeth 72A and 72B may be determined by the dentist and also be recorded to permit the technician to produce a crown that has a color resembling that of the neighboring teeth.

In addition to general physical structure of such a teeth model, the colors of the neighboring teeth 72A and 72B may be determined by the dentist and also recorded to permit the technician to produce a crown that has a color resembling that of the neighboring teeth.

Turning back to FIG. 3, a second finish line data is obtained, after receiving the dentist input, at step 330. The second finish line data is used, in 340, for updating the first finish line data. The updating comprises defining a portion of the finish line not defined in the first finish line (for example, in a 'knife edge' case) or changing a portion of the first finish line. The updated data is further imposed on the dentition image.

The three dimensional virtual teeth model includes at least the preparation, preferably the preparation with neighboring teeth. Typically, however, although not exclusively, the virtual teeth model includes also teeth of the jaw opposite the preparation region. Occasionally, although not necessarily, the virtual teeth model may also include all teeth of both jaws.

The teeth model, and particularly the region thereof that includes the preparation, is typically manipulable such that the virtual teeth model may be displayed and visualized from different angles.

The data for the virtual teeth model may be obtained by a variety of methods, such as that described in PCT Application No. PCT/IL96/00036 (publication No. WO97/03620) and in PCT Application No. PCT/IL99/00431 (publication No. WO00/08415). The virtual three-dimensional image may be manipulated, for example, in a manner described in PCT Application No. PCT/IL99/00577 (publication No. WO00/25677).

The generation of the finish line data can be obtained in any of the known manners. For example, the finish line may be drawn by moving a cursor, by moving a stylus on a touch-sensitive screen or pad, etc. By another example, the line may be drawn by indicating a series of dots while the software then automatically connects the dots into one continuous finish line.

The finish line data can be also obtained in a fully automated manner, for example as described in U.S. Pat. No. 5,417,572. Based on data indicating the 3D shape of the surface of the preparation, a train of points in the margin area is determined by calculations, and the finish line is determined by plotting the train of points on a developed view of the surface. In determining the train of points, a reference line (e.g. a central axis 22 of the 3D shape of the preparation is determined. Several crossing lines between the surface that includes the reference line and the curved plane constituting the shape of the preparation are considered, and the distances between the reference line and corresponding points onto the crossing lines are calculated. Then the inclination between the adjacent points of the adjacent crossing lines is determined. Based on the above-explained calculation, the margin area is defined at a point where the variation of the inclination exceeds a certain value.

Be the method of generating the finish line as it may be, the visual representation of the finish line data is associated with the visual representation of the 3D model such that the digital image of the model will include the finish line data. The dentist is then provided with a digital image of the patient's dentition that includes the generated finish line.

This visual model can be rendered to the dentist in several manners. For example, the dentist is provided with a 3D image of the preparation and its surroundings wherein the finish line is marked, for example, by a colored line. The dentist can be allowed to enlarge the image and to manipulate it for better viewing of the model. The dentist can further be provided with 2D images of cross-sections of the preparation.

The dentist can input his instructions for example by moving a cursor to draw the finish line, by moving a stylus on a touch-sensitive screen or pad, etc. By another example, the dentist can indicates a series of dots onto the 3D or the 2D images, while the software then automatically connects the dots into one continuous finish line.

The finish line obtained according to the present invention may serve as an input in constructing a physical crown, preferably in a CAD/CAM environment. For example, the virtual image with the drawn finish line may be electronically transmitted to the lab that constructs the physical crown and when such image is displayed to the technician and based on such a display, the technician may then identify the finish line on the working cast before him.

The display is typically a computerized display provided with software permitting the technician to visualize the virtual image from different angles. As will be appreciated, the invention is not limited to any specific display means and any means for presenting the image such as, for example, in a printed format, on a computer display screen, etc., may be employed in accordance with the invention.

In accordance with another embodiment of the invention, the technician may use a virtual model with the finish line marked therein by the dentist to construct a virtual crown to be fitted over the virtual tooth preparation. Once a good crown fitting is determined, the virtual crown so obtained may be used as guidance for constructing a real life physical crown. The guidance may be a visual guidance, although, in accordance with one embodiment, digital data representative of the three dimensional structure of the virtual crown is generated and this may be fed into a computer-controlled apparatus that automatically constructs the crown based on such data.

Figure 5:
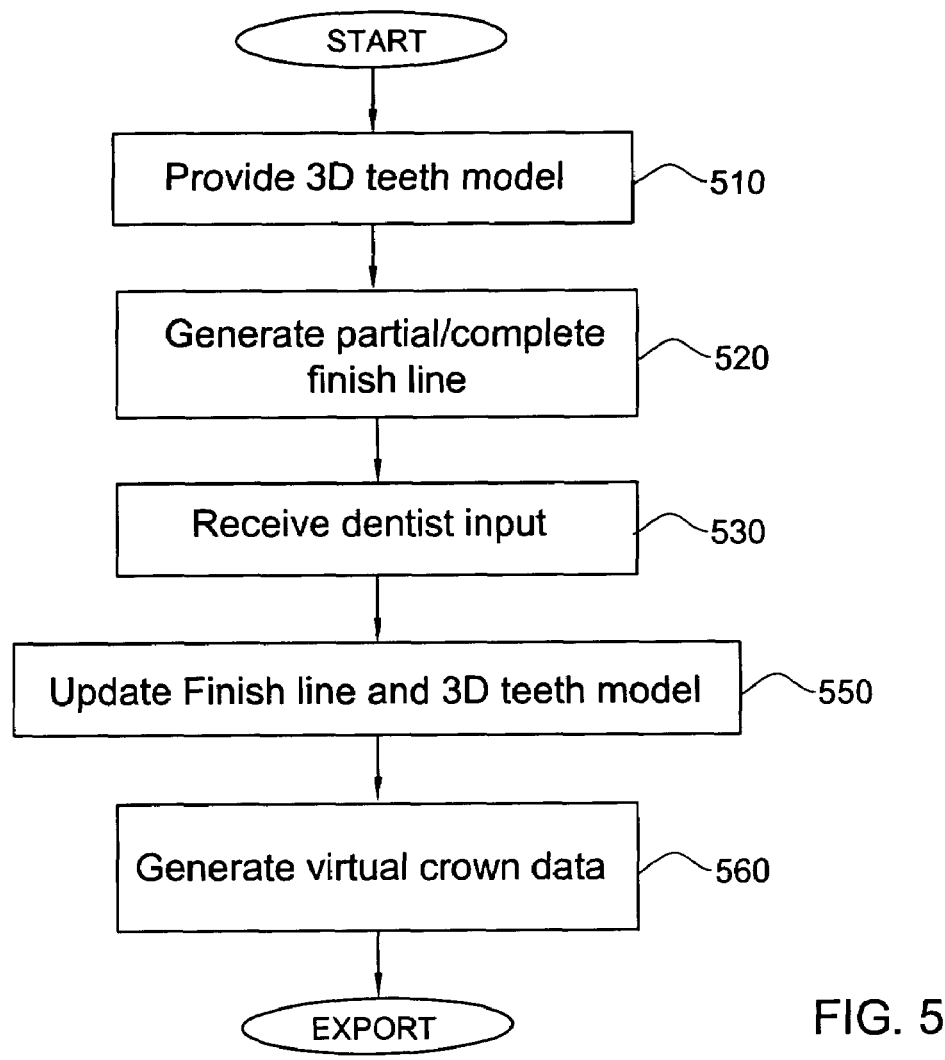
FIG. 5 is a schematic representation of a flow chart showing the virtual construction of a crown to obtain digital crown data.
Figure 6:
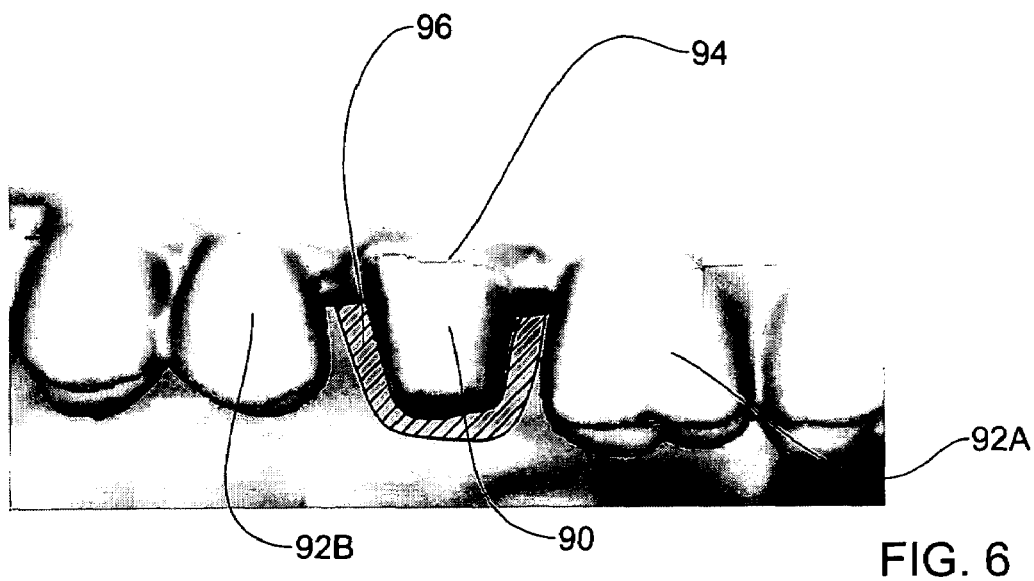
FIG. 6 shows a three dimensional virtual image, similarly as FIG. 4, with an added crown.

Reference is now being made to FIG. 5 showing, by way of a schematic blocked diagram, a method for the construction of a virtual crown to generate digital data representative of such a virtual crown. In FIG. 5, elements with the same function as in FIG. 3 were given the same reference numeral shifted by 200. After a finish line is defined by the dentist, (at 530) and associated with the 3D model (at 550), a virtual crown is constructed (at 550). This may be done manually, according to some embodiments, or may be an automatic procedure carried out by a dedicated software utility. Following such construction, a virtual crown data is generated (at 560) and such data may then be exported to a CNC device for constructing a physical crown. Reference is now being made to FIG. 6. The same reference numerals used in FIG. 4 shifted by 20 are used to designate like components. As can be seen in FIG. 6, a virtual crown 96 is fitted on preparation 90.

It should be understood that the methods of the present invention, as exemplified with reference to FIGS. 3 and 5, are best implemented in distributed systems, like the ones shown in FIGS. 1 and 2, but are not limited to the architectures shown hereto.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

The invention claimed is:

1. A computer-based prosthodontic method for enabling a dental practitioner to define a finish line of a dental prosthesis of at least one tooth to be fitted over a tooth preparation, comprising:
   (One) providing a three-dimensional (3D) digital data relating to the patient's dentition, said 3D data includes data representative of the surface topology of said preparation and its surroundings;

(Two) generating first finish line data representative of at least a portion of said finish line and superimposing an image of said finish line on an image of said dentition;

(Three) obtaining second finish line data determined on the basis of input received from a dental practitioner; and (Four) using said second finish line data to update said first finish line data and superimposing the updated data on the dentition image.

2. A method according to claim 1, wherein the updating of the first finish line data comprises defining a portion of the finish line not defined in said first finish line data or changing a portion of said first finish line data.

3. A method according to claim 1, wherein the second finish line data is generated by virtually drawing a line at the apical limit of the preparation.

4. A method according to claim 3, wherein the line is drawn in a continuous fashion.

5. A method according to claim 3, wherein the line is drawn by marking dots in small intervals and then forming a line by automatically connecting the dots to one another.

6. A method according to claim 1, wherein the defined finish line is used as an input in constructing a crown.

7. A computer-based method for constructing a crown to be fitted on a tooth preparation in a subject, the method comprising defining a finish line on said preparation to obtain finish line data and employing said data in constructing the crown; the method being characterized in that defining the finish line comprises:

(One) providing a three-dimensional (3D) digital data relating to the patient's dentition, said 3D data includes data representative of the surface topology of said preparation and its surroundings;

(Two) generating first finish line data representative of at least a portion of said finish line and superimposing an image of said finish line on an image of said dentition;

(Three) obtaining second finish line data on a finish line determined on the basis of input received from a dental practitioner; and (Four) using said second finish line data to update said first finish line data and superimposing the updated data on the dentition image.

8. A method according to claim 7, wherein a virtual image of the preparation with a defined finish line is presented on a suitable display medium.

9. A method according to claim 7, comprising:
constructing a virtual crown and virtually fitting said crown on said preparation in said virtual teeth;
generating digital data representing the three dimensional structure of the virtual crown;
employing said digital data to construct a physical crown for fitting on a tooth preparation in a patient.

10. A server utility of a computer-based system, for enabling a dental practitioner to define a finish line of a dental prosthesis of at least one tooth to be fitted over a tooth preparation, said utility comprising:

(a) a processor;

(b) a memory coupled to the processor for storing a three-dimensional (3D) digital data relating to the patient's dentition, the 3D data including data representative of the surface topology of the preparation and its surroundings;

(c) a dedicated utility coupled to or integrated with the processor for generating a first finish line data representative of at least a portion of said finish line and superimposing an image of said finish line on an image of said dentition; and (d) a network interface coupled to the processor for transmitter to a dental practitioner computerized device at least a portion of the 3D digital data and the first finish line data and for receiving from the practitioner device data representative of a second finish line determined on the basis of practiotioner input, wherein the second finish line data is used to update the first finish line data.

11. A computer-based program storage device readable by machine, tangibly embodying a program of instructions executable by the machine to perform method steps for constructing a crown to be fitted on a tooth preparation in a subject, the method comprising defining a finish line on said preparation to obtain finish line data and employing said data in constructing the crown; the method being characterized in that defining the finish line comprises:

(a) providing a three-dimensional (3D) digital data relating to the patient's dentition, said 3D data includes data representative of the surface topology of said preparation and its surroundings;

(b) generating first finish line data representative of at least a portion of said finish line and superimposing an image of said finish line on an image of said dentition;

(c) obtaining second finish line data on a finish line determined on the basis of input received from a dental practitioner; and (d) using said second finish line data to update said first finish line data and superimposing the updated data on the dentition image.

* * * * *

(12) INTER PARTES REVIEW CERTIFICATE (2102nd)
United States Patent (10) Number: US 7,112,065 K1
Kopelman et al. (45) Certificate Issued: Jun. 11, 2021

(54) METHOD FOR DEFINING A FINISH LINE OF A DENTAL PROSTHESIS

(75) Inventors: Avi Kopelman; Eldad Taub

(73) Assignee: ALIGN TECHNOLOGY, INC.

Trial Number:

IPR2019-00132 filed Nov. 7, 2018

Inter Partes Review Certificate for:

Patent No.: 7,112,065
Issued: Sep. 26, 2006
Appl. No.: 10/623,707
Filed: Jul. 22, 2003

The results of IPR2019-00132 are reflected in this inter partes review certificate under 35 U.S.C. 318(b).

INTER PARTES REVIEW CERTIFICATE
U.S. Patent 7,112,065 K1
Trial No. IPR2019-00132
Certificate Issued Jun. 11, 2021

AS A RESULT OF THE INTER PARTES REVIEW PROCEEDING, IT HAS BEEN DETERMINED THAT:

Claims 1-9 and 11 are cancelled.

\* \* \* \* \*